(12) United States Patent
Umeno et al.

(10) Patent No.: US 9,156,163 B2
(45) Date of Patent: Oct. 13, 2015

(54) ROBOT SYSTEM

(71) Applicant: KABUSHIKI KAISHA YASKAWA DENKI, Kitakyushu-shi (JP)

(72) Inventors: Makoto Umeno, Kitakyushu (JP); Tomoyuki Horiuchi, Kitakyushu (JP); Takashi Suyama, Kitakyushu (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 134 days.

(21) Appl. No.: 13/934,240

(22) Filed: Jul. 3, 2013

(65) Prior Publication Data

US 2014/0025202 A1    Jan. 23, 2014

(30) Foreign Application Priority Data

Jul. 19, 2012   (JP) ................. 2012-161017

(51) Int. Cl.
| | |
|---|---|
| *B25J 9/16* | (2006.01) |
| *B25J 9/00* | (2006.01) |
| *B04B 5/04* | (2006.01) |
| *B04B 13/00* | (2006.01) |
| *G01N 35/00* | (2006.01) |
| *B04B 11/04* | (2006.01) |

(52) U.S. Cl.
CPC .............. *B25J 9/1612* (2013.01); *B25J 9/0087* (2013.01); *G01N 35/0099* (2013.01); *B04B 5/0414* (2013.01); *B04B 13/00* (2013.01); *B04B 2011/046* (2013.01); *G01N 2035/00495* (2013.01)

(58) Field of Classification Search
CPC ................ G01N 35/0099; G01N 2035/00495; B25J 9/0087; B04B 2011/046; B04B 13/00; B04B 5/0414; B04B 5/0421
See application file for complete search history.

(56) References Cited

U.S. PATENT DOCUMENTS 6,758,803 B2 * 7/2004 Jang ................................ 494/10
2004/0184958 A1   9/2004 Itoh

FOREIGN PATENT DOCUMENTS

| EP | 0569115 | 11/1993 |
|---|---|---|
| EP | 2458387 | 5/2012 |
| JP | 03-073247 | 3/1991 |
| JP | 08-324755 | 12/1996 |
| JP | 2000-176316 | 6/2000 |

(Continued)

OTHER PUBLICATIONS

Extended European Search Report for corresponding EP Application No. 13173743.9-1712, Nov. 25, 2013.

(Continued)

*Primary Examiner* — Khoi Tran
*Assistant Examiner* — Robert Nguyen
(74) *Attorney, Agent, or Firm* — Mori & Ward, LLP

(57) ABSTRACT

A robot system includes: a robot arm; a robot hand provided on the robot arm; a contact unit provided on the robot hand for rotating a rotation body of a rotation device which includes the rotation body capable of housing a work and a fixed part rotatably supporting the rotation body and which performs a predetermined process on the work; a detection unit configured to detect a detection target part provided on the rotation body; and a first control unit configured to control operation of the robot arm and the robot hand so that the contact unit rotates the rotation body up to a predetermined rotational position according to a result of detecting the detection target part by the detection unit.

10 Claims, 15 Drawing Sheets

(56) References Cited

FOREIGN PATENT DOCUMENTS

| | | |
|---|---|---|
| JP | 2004-230329 | 8/2004 |
| JP | 2008-000849 | 1/2008 |
| JP | 2011-251828 | 12/2011 |

OTHER PUBLICATIONS

Japanese Office Action for corresponding JP Application No. 2012-161017, Dec. 19, 2013.

Chinese Office Action for corresponding CN Application No. 201310299492.4, Feb. 4, 2015.

* cited by examiner

ROBOT SYSTEM

CROSS-REFERENCE TO RELATED APPLICATION

The application claims priority under 35 U.S.C. §119 to Japanese Patent Application No. 2012-161017 filed on Jul. 19, 2012, the entire disclosure of which is hereby incorporated by reference.

BACKGROUND

1. Technical Field

An embodiment of the present disclosure relates to a robot system.

2. Related Art

JP-A-2011-251828 discloses a processing system including a robot system.

SUMMARY

A robot system according to an aspect of the present disclosure includes: a robot arm; a robot hand provided on the robot arm; a contact unit provided on the robot hand for rotating a rotation body of a rotation device which includes the rotation body capable of housing a work and a fixed part rotatably supporting the rotation body and which performs a predetermined process on the work; a detection unit configured to detect a detection target part provided on the rotation body; a first control unit configured to control operation of the robot arm and the robot hand so that the contact unit rotates the rotation body up to a predetermined rotational position according to a result of detecting the detection target part by the detection unit; and a second control unit configured to control operation of the robot arm and the robot hand so that the work is installed at a predetermined work set part of the rotation body stopping at the predetermined rotational position or the work is removed from the work set part.

DETAILED DESCRIPTION

Figure 1:
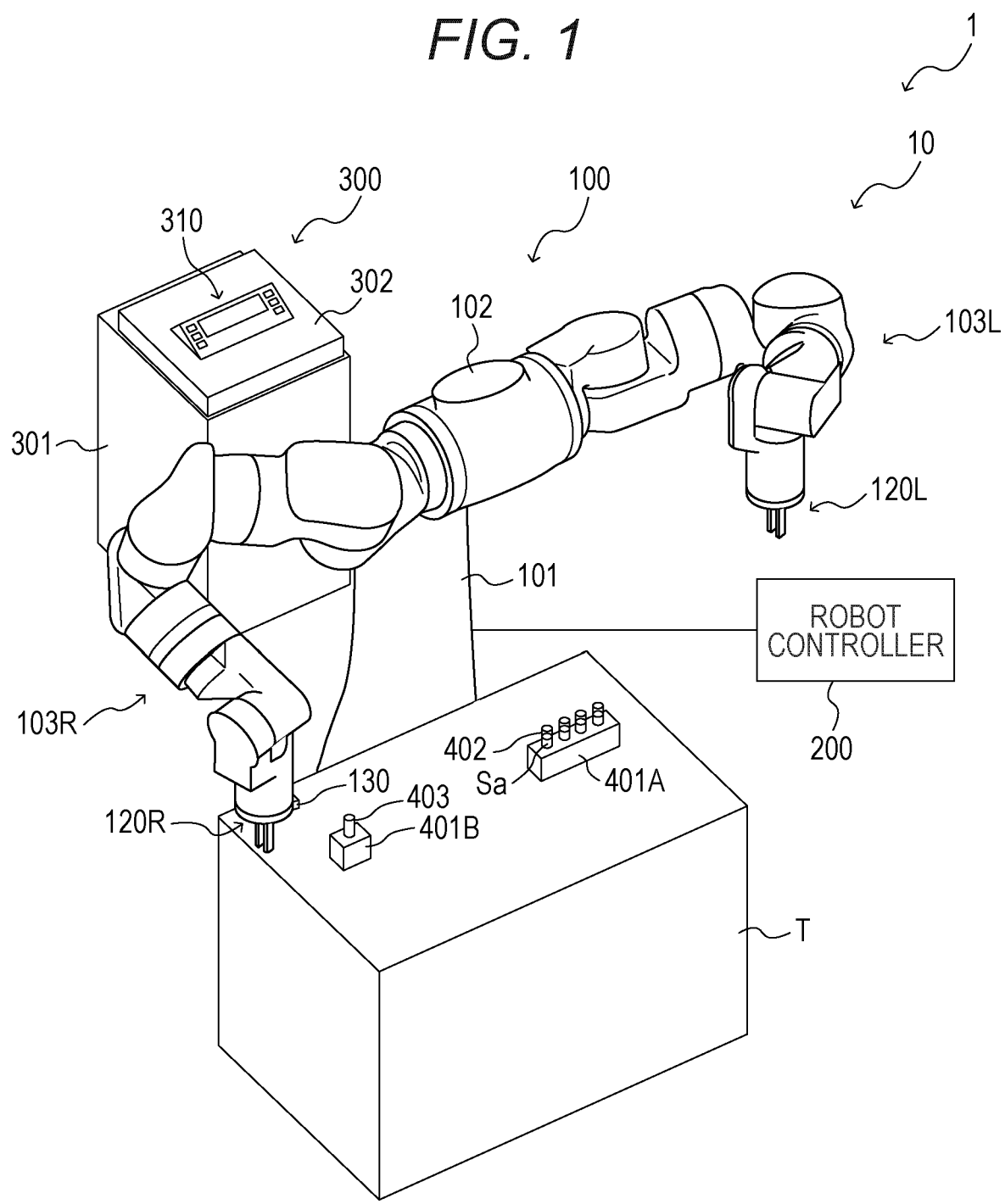
FIG. 1 is a system configuration diagram illustrating an example of an entire configuration of a robot system according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An embodiment is hereinafter described with reference to the drawings. In this embodiment, a series of jobs to be executed by a robot system is described. The jobs include a job of inserting a tube into an insertion hole provided on a rotor of a centrifugal separator and a job of removing the tube from the insertion hole.

First, with reference to FIG. 1, an example of the entire configuration of a robot system of this embodiment is described.

As depicted in FIG. 1, a robot system 1 according to this embodiment includes a robot system 10 and a centrifugal separator (also called a centrifugal machine, a centrifuge, a centrifugal device, or the like) 300. The centrifugal separator 300 corresponds to a rotation device.

The robot system 10 includes a robot main body 100 and a robot controller 200. The robot main body 100 and the robot controller 200 are connected with or without a wire to communicate with each other. The robot main body 100 may include the robot controller therein.

The robot main body 100 includes a base stand 101, a trunk part 102, and two arms 103L and 103R (robot arms). The robot main body 100 is a so-called double-arm robot. An end of the arm 103L is provided with a left hand (also called a tool, an end effector, or the like) 120L. Similarly, an end of the arm 103R is provided with a right hand (also called a tool, an end effector, or the like) 120R. The hands 120L and 120R correspond to robot hands. The hand may alternatively be provided for a part other than the end of the arm. The robot main body 100 is later described more specifically.

The right hand 120R is provided with a sensor 130 (detection unit). The position of the sensor 130 at the right hand 120R is not limited to that depicted in FIG. 1, but may be another position. The sensor 130 is not necessarily fixed directly on the right hand 120R. The sensor 130 may be fixed (connected) indirectly on the right hand 120R via an appropriate member. Instead of, or in addition to the right hand 120R, the left hand 120L may be provided with the sensor 130. The sensor 130 is later described in detail.

The robot controller 200 includes a computer including, for example, a calculator, a memory device, an input device, and the like. The robot controller 200 controls over the entire operation of the robot main body 100. The robot controller 200 is later described more specifically.

A table T is disposed near the robot main body 100. Two racks 401A and 401B are disposed at appropriate positions on the table T.

The rack 401A houses a tube (centrifugal precipitation tube, centrifugal settler, centrifuge tube, sedimentation tube, etc.) 402. The tube 402 can be inserted into an insertion hole 306 provided on a rotor 305 of the centrifugal separator 300 to be described later. The tube 402 corresponds to a vessel to be processed, and a work. The tube 402 is not particularly limited as long as the tube 402 is the vessel that can be inserted into the insertion hole 306. The tube 402 may be, for example, a conical tube or a microtube.

Figure 2:
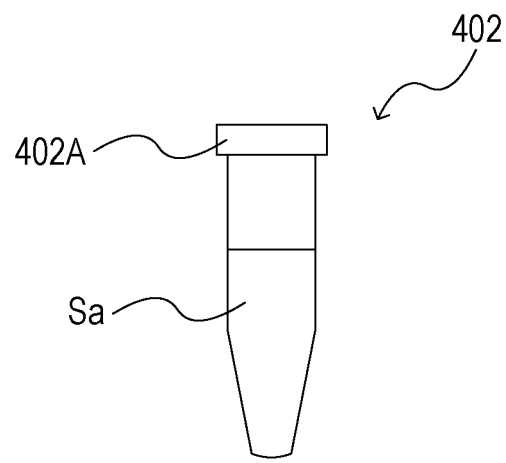
FIG. 2 is a plan diagram illustrating an example of a configuration of a tube.

FIG. 2 depicts an example of the configuration of the tube 402. As depicted in FIG. 2, the tube 402 includes an opening (not shown) formed at an upper part thereof, and a lid 402A. The lid 402A is capable of covering and uncovering the opening. The configuration of the tube 402 is not limited to this example. A sample Sa (body to be separated) is housed in the tube 402. The sample Sa is a target which is subjected to centrifugal separation in the centrifugal separator 300.

The tube 402 is held by one hand 120 (for example, the left hand 120L) of the robot main body 100. The tube 402 is inserted into the particular insertion hole 306 provided on the rotor 305 of the centrifugal separator 300 to be later described (the details are described later).

The rack 401B houses an insertion tool 403. The insertion tool 403 can be inserted into the insertion hole 306 provided on the rotor 305 of the centrifugal separator 300 to be later described. The insertion tool 403 is not particularly limited as long as it can be inserted into the insertion hole 306.

Figure 3:
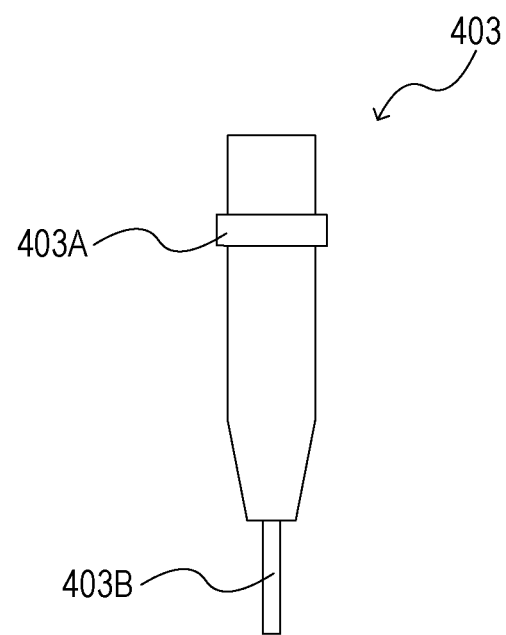
FIG. 3 is a plan diagram illustrating an example of a configuration of an insertion tool.

FIG. 3 depicts an example of the configuration of the insertion tool 403. As depicted in FIG. 3, the insertion tool 403 has an approximately cylindrical shape as a whole. This insertion tool 403 is provided with a flange part 403A provided at an intermediate part in its longitudinal direction, and an end part 403B having a smaller outer diameter than the inner diameter of the insertion hole 306. The configuration of the insertion tool 403 is not limited to this example.

This insertion tool 403 is held by one hand 120 (for example, the right hand 120R) of the robot main body 100. A part of the end part 403B of the insertion tool 403 is inserted into the particular insertion hole 306 provided on the rotor 305 of the centrifugal separator 300 to be described later. The part of the end part 403B is in contact with an inner peripheral surface of the insertion hole 306 (the details are described later). Holding the insertion tool 403 by the hand 120 can be equivalent to providing the insertion tool 403 on the hand 120. Therefore, the insertion tool 403 held by the hand 120 corresponds to a contact unit.

The centrifugal separator 300 is a device for centrifugally separating the sample Sa. That is, the sample Sa is housed in the tube 402, and the tube 402 is inserted into the insertion hole 306 provided on the rotor 305 to be described later. The centrifugal separator 300 applies a centrifugal force on the sample Sa in the tube 402 inserted into the insertion hole 306. Thus, the centrifugal separator 300 separates or fractionates the components (dispersoid) contained in the sample Sa. In other words, the centrifugal separation corresponds to the predetermined processing. The centrifugal separator 300 includes a casing 301 (fixed part) and a lid 302, which are described later. The lid 302 is rotatably connected to the casing 301. An operation panel 310 including a display unit, an input unit, and the like is provided at an upper part of the lid 302 capable of covering and uncovering an opening 303A of a bowl 303 provided on the casing 301.

Figure 4:
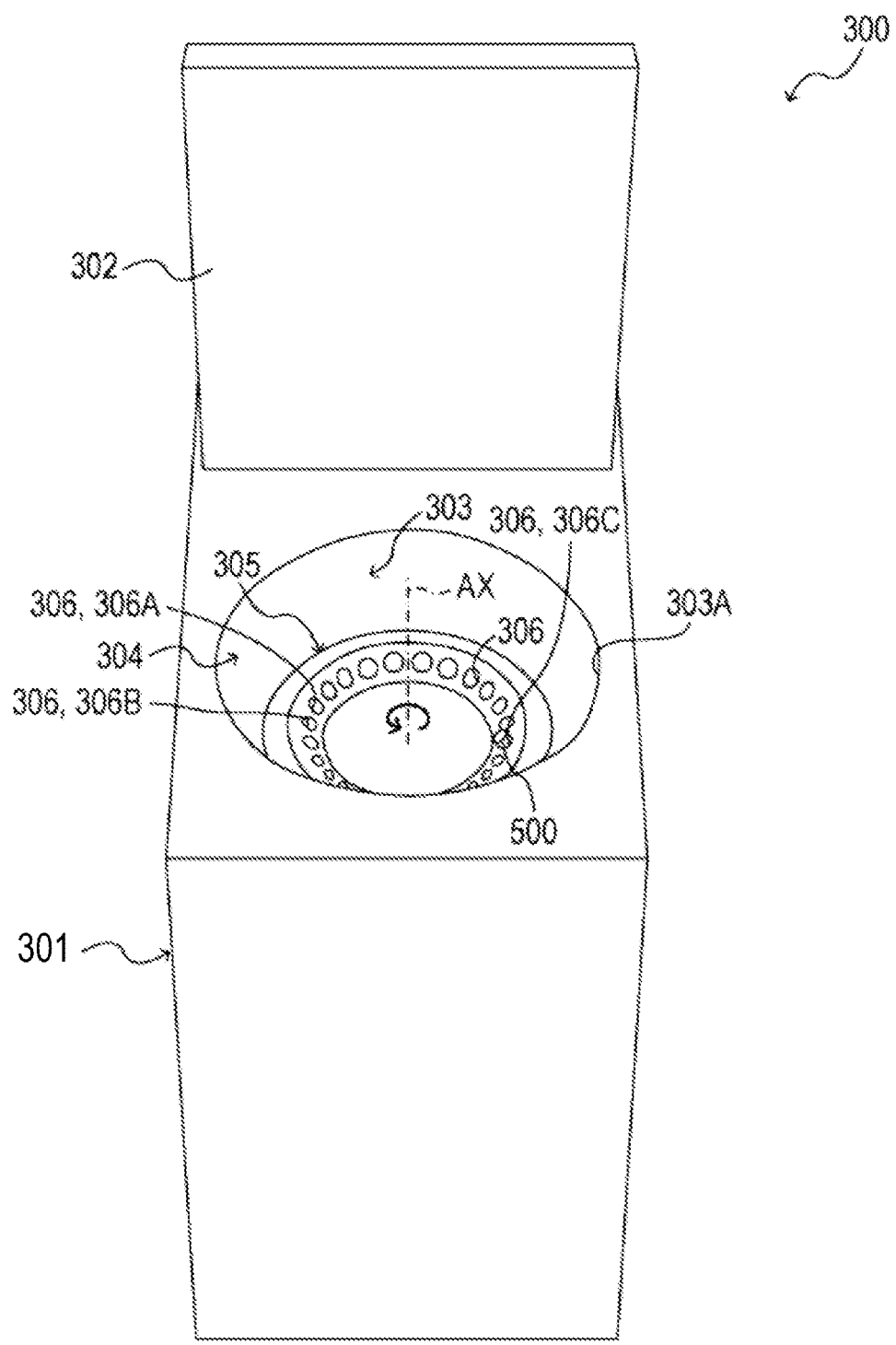
FIG. 4 is a perspective diagram illustrating an internal configuration of a casing of a centrifugal separator.

FIG. 4 depicts an example of an internal configuration of the casing 301 of the centrifugal separator 300. As depicted in FIG. 4, the casing 301 of the centrifugal separator 300 is provided with the bowl 303. The rotor 305 (rotation body) with an approximately circular shape in a plan view is provided in a rotor chamber 304 including the bowl 303. The rotor 305 is connected to a rotating shaft (not shown) of a motor (not shown) provided inside the casing 301. The rotor 305 is supported by the casing 301 so that the rotor 305 can be rotated around an axis of rotation AX by the motor. In the centrifugal separator 300, the position at which the rotor 305 stops (rotational position) can vary (is not constant) every time the rotation ends (that is, every time the centrifugal separation process ends). A plurality of (24 in this example) insertion holes 306 (insertion ports) with an approximately circular shape is provided on the rotor 305 along its circumferential direction. The insertion hole 306 can have the tube 402 housed therein. The number of insertion holes 306 in the rotor 305 is not limited to 24. Moreover, the configuration of the centrifugal separator 300 is not limited to this example.

When the rotor 305 has the 24 insertion holes 306, the rotor 305 can have 24 tubes 402 at the maximum. Therefore, the centrifugal separator 300 can process 24 samples Sa at the maximum in one operation. However, in this embodiment, one tube 402 is provided for the rotor 305 and the centrifugal separator 300 processes one sample Sa in one operation.

Among the 24 insertion holes 306, a positioning member (detection target part) 500 is inserted in advance into one appropriate insertion hole 306C (third insertion port). Note that, before the centrifugal separation process of the centrifugal separator 300 is started, the robot main body 100 may have the positioning member 500 inserted into the insertion hole 306C. The state in which the positioning member 500 is inserted in advance into the insertion hole 306C can be regarded as the state in which the positioning member 500 is provided on the rotor 305. Therefore, the positioning member 500 inserted in advance into the insertion hole 306C corresponds to the detection unit. The positioning member 500 is not particularly limited as long as the member 500 is a member that can be inserted into the insertion hole 306. The positioning member 500 may be, for example, a tube. In this embodiment, the poisoning member 500 serves as a tube (dummy tube) not having the sample Sa. The poisoning member 500 is also referred to as a tube 500 below.

Figure 5:
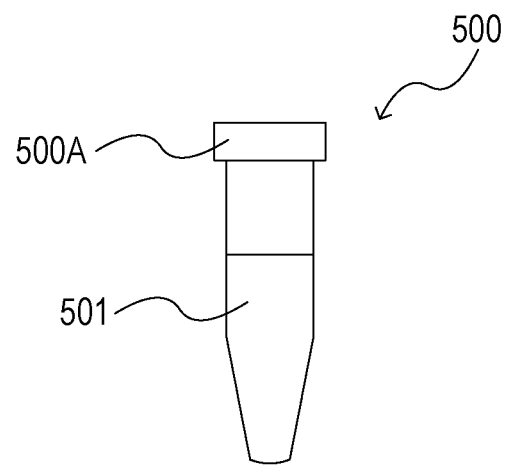
FIG. 5 is a plan diagram illustrating an example of a configuration of a tube serving as a positioning member.

FIG. 5 depicts an example of the tube 500. As depicted in FIG. 5, the tube 500 includes an opening (not shown) formed at its upper part, and a lid 500A. The lid 500A can cover and uncover the opening. The configuration of the tube 500 is not limited to this example. An appropriate object (liquid or solid) 501 is housed in the tube 500. The sum of the weight of the tube 500 and the weight of the object 501 inside is preferably substantially equal to the sum of the weight of the tube 402 and the weight of the sample Sa inside.

The appropriate one insertion hole 306B (second insertion port) among the 24 insertion holes 306 is determined in advance as the sample set part (work set part) where the tube 402 having the sample Sa housed therein is inserted. In this embodiment, the insertion hole 306B is provided at the position facing the insertion hole 306C. This insertion hole 306B is determined in advance as the sample set part. The sample set part is not limited to the insertion hole 306B at the position facing the insertion hole 306C. However, in consideration of the weight balance of the rotor 305, the sample set part is preferably the insertion hole 306B.

The appropriate one insertion hole 306A (first insertion port) among the 24 insertion holes 306 is determined in advance as the insertion hole where the insertion tool 403 is inserted. In this embodiment, the insertion hole 306A is provided next to the insertion hole 306B clockwise. This insertion hole 306A is determined in advance as the insertion hole where the insertion tool 403 is inserted. The insertion hole where the insertion tool 403 is inserted is not limited to the insertion hole 306A next to the insertion hole 306B clockwise.

Figure 6A:
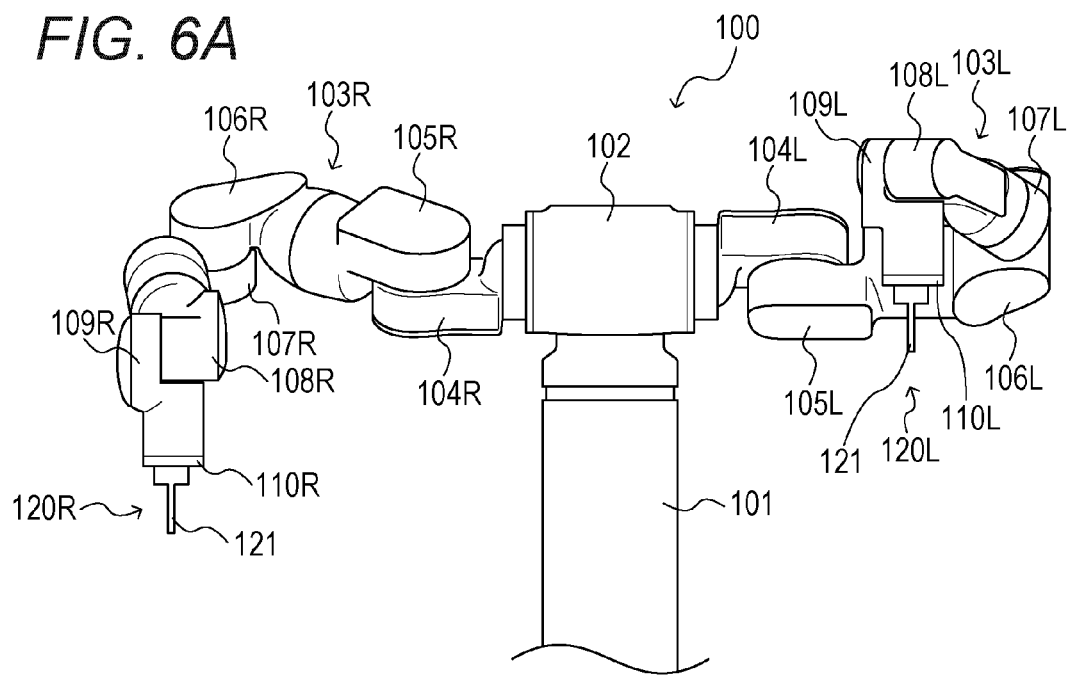
FIG. 6A is a front diagram illustrating an example of a configuration of a robot main body.
Figure 6B:
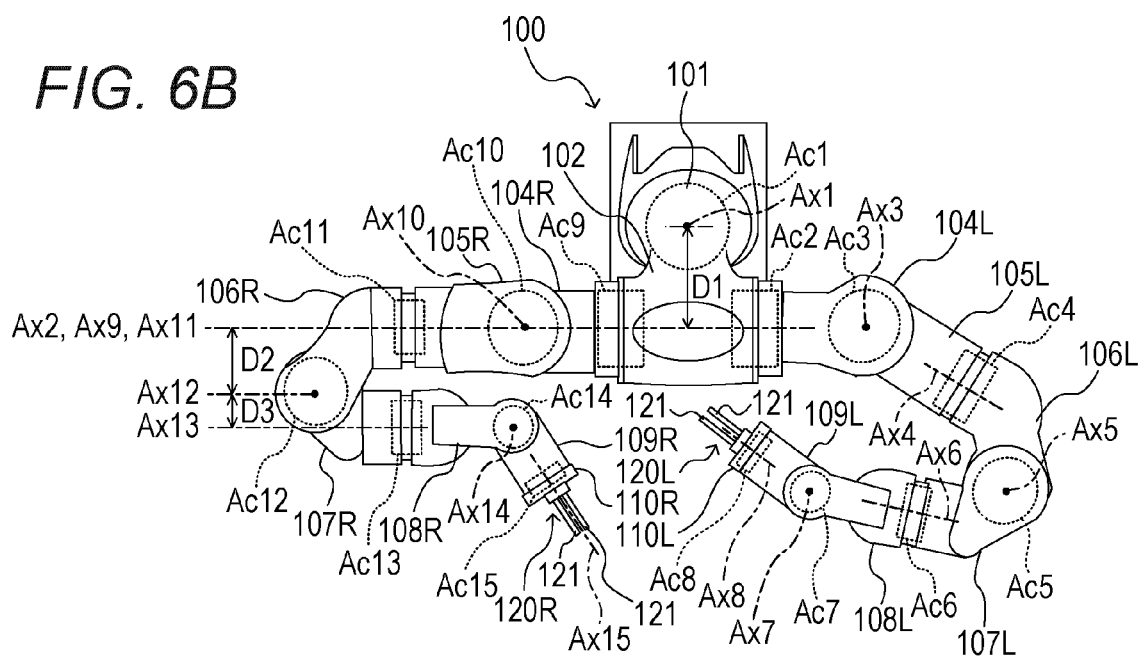
FIG. 6B is a top diagram thereof.

Next, with reference to FIGS. 6A and 6B, one example of the configuration of the robot main body 100 is described.

As depicted in FIGS. 6A and 6B, the base stand 101 of the robot main body 100 is fixed to an installation surface (such as a floor) with an anchor bolt or the like (not shown).

The trunk part 102 of the robot main body 100 has a first joint part. The first joint part has a first actuator Ac1. The first actuator Ac1 rotates and drives the trunk part 102 around a first rotation axis Ax1, which is approximately perpendicular to the installation surface. Therefore, the trunk part 102 is installed on the base stand 101 via the first joint part so that the trunk part 102 can be rotated around the first rotation axis Ax1. One end of the trunk part 102 supports the arm 103L, while the other end thereof supports the arm 103R. The trunk part 102 is rotated around the first rotation axis Ax1 by the first actuator Ac1. This turns the entire arms 103L and 103R.

The arm 103L has a shoulder part 104L, an upper arm A part 105L, an upper arm B part 106L, a lower arm part 107L, a wrist A part 108L, a wrist B part 109L, and a flange 110L. These parts are rotated and driven by second to eighth actuators Ac2 to Ac8, respectively. The second to eighth actuators are provided at second to eighth joint parts of the arm 103L, respectively.

The shoulder part 104L is rotatably connected to the trunk part 102 via the second joint part. The shoulder part 104L is rotated around a second rotation axis Ax2 which is approximately parallel to the installation surface by the second actuator Ac2 provided at the second joint part.

The upper arm A part 105L is turnably connected to the shoulder part 104L via the third join part. The upper arm A part 105L is turned around a third rotation axis Ax3 which is approximately perpendicular to the second rotation axis Ax2 by the third actuator Ac3 provided at the third joint part.

The upper arm B part 106L is rotatably connected to the upper arm A part 105L via the fourth joint part. The upper arm B part 106L is rotated around a fourth rotation axis Ax4 which is approximately perpendicular to the third rotation axis Ax3 by the fourth actuator Ac4 provided at the fourth joint part.

The lower arm part 107L is turnably connected to the upper arm B part 106L via the fifth joint part. The lower arm part 107L is turned around a fifth rotation axis Ax5 which is approximately perpendicular to the fourth rotation axis Ax4 by the fifth actuator Ac5 provided at the fifth joint part.

The wrist A part 108L is rotatably connected to the lower arm part 107L via the sixth joint part. The wrist A part 108L is rotated around a sixth rotation axis Ax6 which is approximately perpendicular to the fifth rotation axis Ax5 by the sixth actuator Ac6 provided at the sixth joint part.

The wrist B part 109L is turnably connected to the wrist A part 108L via the seventh joint part. The wrist B part 109L is turned around a seventh rotation axis Ax7 which is approximately perpendicular to the sixth rotation axis Ax6 by the seventh actuator Ac7 provided at the seventh joint part.

The flange 110L is rotatably connected to the wrist B part 109L via the eighth joint part. The flange 110L is rotated around an eighth rotation axis Ax8 which is approximately perpendicular to the seventh rotation axis Ax7 by the eighth actuator Ac8 provided at the eighth joint part.

Moreover, an end of the flange 110L is provided with the left hand 120L. This left hand 120L is rotated around the eighth rotation axis Ax8 in conjunction with the rotation of the flange 110L around the eighth rotation axis Ax8.

The left hand 120L has two holding members 121 that can move in a direction where the members approach each other or separate from each other. The left hand 120L can hold at least one of the tube 402 and the insertion tool 403 with these two holding members 121. The left hand 120L is not limited to this example. The left hand 120L may have, for example, five finger members. In this case, the left hand 120L may be able to hold at least one of the tube 402 and the insertion tool 403 with these five finger members.

The arm 103R has the configuration similar to that of the arm 103L. In other words, the arm 103R has a shoulder part 104R, an upper arm A part 105R, an upper arm B part 106R, a lower arm part 107R, a wrist A part 108R, a wrist B part 109R, and a flange 110R. These parts are rotated and driven by ninth to fifteenth actuators Ac9 to Ac15, respectively. The ninth to fifteenth actuators are provided at ninth to fifteenth joint parts of the arm 103R, respectively.

The shoulder part 104R is rotatably connected to the trunk part 102 via the ninth joint part. The shoulder part 104R is rotated around a ninth rotation axis Ax9 which is approximately parallel to the installation surface by the ninth actuator Ac9 provided at the ninth joint part.

The upper arm A part 105R is turnably connected to the shoulder part 104R via the tenth joint part. The upper arm A part 105R is turned around a tenth rotation axis Ax10 which is approximately perpendicular to the ninth rotation axis Ax9 by the drive of the tenth actuator Ac10 provided at the tenth joint part.

The upper arm B part 106R is rotatably connected to the upper arm A part 105R via the eleventh joint part. The upper arm B part 106R is rotated around an eleventh rotation axis Ax11 which is approximately perpendicular to the tenth rotation axis Ax10 by the eleventh actuator Ac11 provided at the eleventh joint part.

The lower arm part 107R is turnably connected to the upper arm B part 106R via the twelfth joint part. The lower arm part 107R is turned around a twelfth rotation axis Ax12 which is approximately perpendicular to the eleventh rotation axis Ax11 by the twelfth actuator Ac12 provided at the twelfth joint part.

The wrist A part 108R is rotatably connected to the lower arm part 107R via the thirteenth joint part. The wrist A part 108R is rotated around a thirteenth rotation axis Ax13 which is approximately perpendicular to the twelfth rotation axis Ax12 by the thirteenth actuator Ac13 provided at the thirteenth joint part.

The wrist B part 109R is turnably connected to the wrist A part 108R via the fourteenth joint part. The wrist B part 109R is turned around a fourteenth rotation axis Ax14 which is approximately perpendicular to the thirteenth rotation axis Ax13 by the fourteenth actuator Ac14 provided at the fourteenth joint part.

The flange 110R is rotatably connected to the wrist B part 109R via the fifteenth joint part. The flange 110R is rotated around a fifteenth rotation axis Ax15 which is approximately perpendicular to the fourteenth rotation axis Ax14 by the fifteenth actuator Ac15 provided at the fifteenth joint part.

An end of the flange 110R is provided with the right hand 120R. The right hand 120R is rotated around the fifteenth rotation axis Ax15 in conjunction with the rotation of the flange 110R around the fifteenth rotation axis Ax15.

The right hand 120R has a similar configuration to the left hand 120L. That is, the right hand 120R has the two holding members 121 that can move in a direction where the members approach each other or separate from each other. The right hand 120R can hold at least one of the tube 402 and the insertion tool 403 with these two holding members 121. The right hand 120R is not limited to this example. The right hand 120R may have a different configuration from the left hand 120L. The right hand 120R may have, for example, five finger members. In this case, the right hand 120R may be able to hold at least one of the tube 402 and the insertion tool 403 with these five finger members.

The right hand 120R has the sensor 130 installed as described above (see FIG. 1. The sensor 130 is not depicted in FIGS. 6A and 6B). As described above, the rotor 305 of the centrifugal separator 300 is provided with the insertion hole 306C. This insertion hole 306C has the tube 500 inserted therein. The sensor 130 detects this tube 500. The sensor 130 is not particularly limited as long as the sensor 130 can detect the tube 500 inserted in the insertion hole 306C. The sensor 130 may be, for example, a laser sensor. In this embodiment, the sensor 130 is a laser sensor. The sensor 130 has a light projection unit 131 and a light reception unit 132 (see FIG. 10 and the like). In this sensor 130, the light projection unit 131 projects laser light. The light reception unit 132 receives its reflection light. Thus, the sensor 130 can detect the tube 500 (the details are described later). The detection results of the tube 500 by the sensor 130 are output to the robot controller 200 as sensor signals.

Each of the first to fifteenth actuators Ac1 to Ac15 of the robot main body 100 may include a servo motor including a decelerator, for example. Each of the first to fifteenth actuators Ac1 to Ac15 may include a rotational position sensor (such as an encoder, which is not shown). The rotational position sensor outputs a signal indicating the rotational position information of the first to fifteenth actuators Ac1 to Ac15 to the robot controller 200 for every predetermined calculation cycle.

In this example, the arms 103L and 103R have seven joint parts, i.e., seven degrees of freedom. That is, the arms 103L and 103R have three degrees of freedom in forward movement, three degrees of freedom in rotation, and one degree of freedom in redundancy. Note that the number of degrees of freedom of the arms 103L and 103R is not limited to seven.

As depicted in FIG. 6B, the trunk part 102 is formed so that the parts ranging from the first joint part to the second and ninth joint parts protrude horizontally forward beyond the base stand 101. Thus, the first rotation axis Ax1, and the second rotation axis Ax2 and the ninth rotation axis Ax9 are offset by a length of D1 in a direction approximately parallel to the installation surface. Thus, the space below the shoulder parts 104L and 104R can be used as a working space. Moreover, by rotation of the rotation axis Ax1, the range that the arms 103L and 103R can reach can be expanded.

Moreover, the shape of the upper arm B part 106R is set so that the position of the eleventh rotation axis Ax11 and the position of the twelfth rotation axis Ax 12 are offset by a length of D2 as viewed from top. In addition, the shape of the lower arm part 107R is set so that the position of the twelfth rotation axis Ax12 and the position of the thirteenth rotation axis Ax13 are offset by a length of D3 as viewed from top. Therefore, when the eleventh rotation axis Ax11 and the thirteenth rotation axis Ax13 are approximately perpendicular to each other, the offset length of the eleventh rotation axis Ax11 and the thirteenth rotation axis Ax13 is (D2+D3). Thus, a large clearance between the lower arm part 107R corresponding to the "lower arm" of a person and the upper arm A part 105R and the upper arm B part 106R which correspond to the "upper arm" of a person can be secured when the twelfth joint part corresponding to the "elbow" of a person is bent. As a result, even when the right hand 120R attached at an end of the flange 110R is brought closer to the trunk part 102, the degree of freedom of the operation of the arm 103R can be increased.

Moreover, as for the arm 103L, although not explicitly depicted in FIG. 6B, the shape of the upper arm B part 106L is set so that the position of the fourth rotation axis Ax4 and the fifth rotation axis Ax5 are offset by a length of D2 as viewed from top. The shape of the lower arm part 107L is set so that the position of the fifth rotation axis Ax5 and the sixth rotation axis Ax6 are offset by a length of D3 as viewed from top. As a result, the offset length of the fourth rotation axis Ax4 and the sixth rotation axis Ax6 when the fourth rotation axis Ax4 and the sixth rotation axis Ax6 are approximately parallel to each other is (D2+D3).

Figure 7:
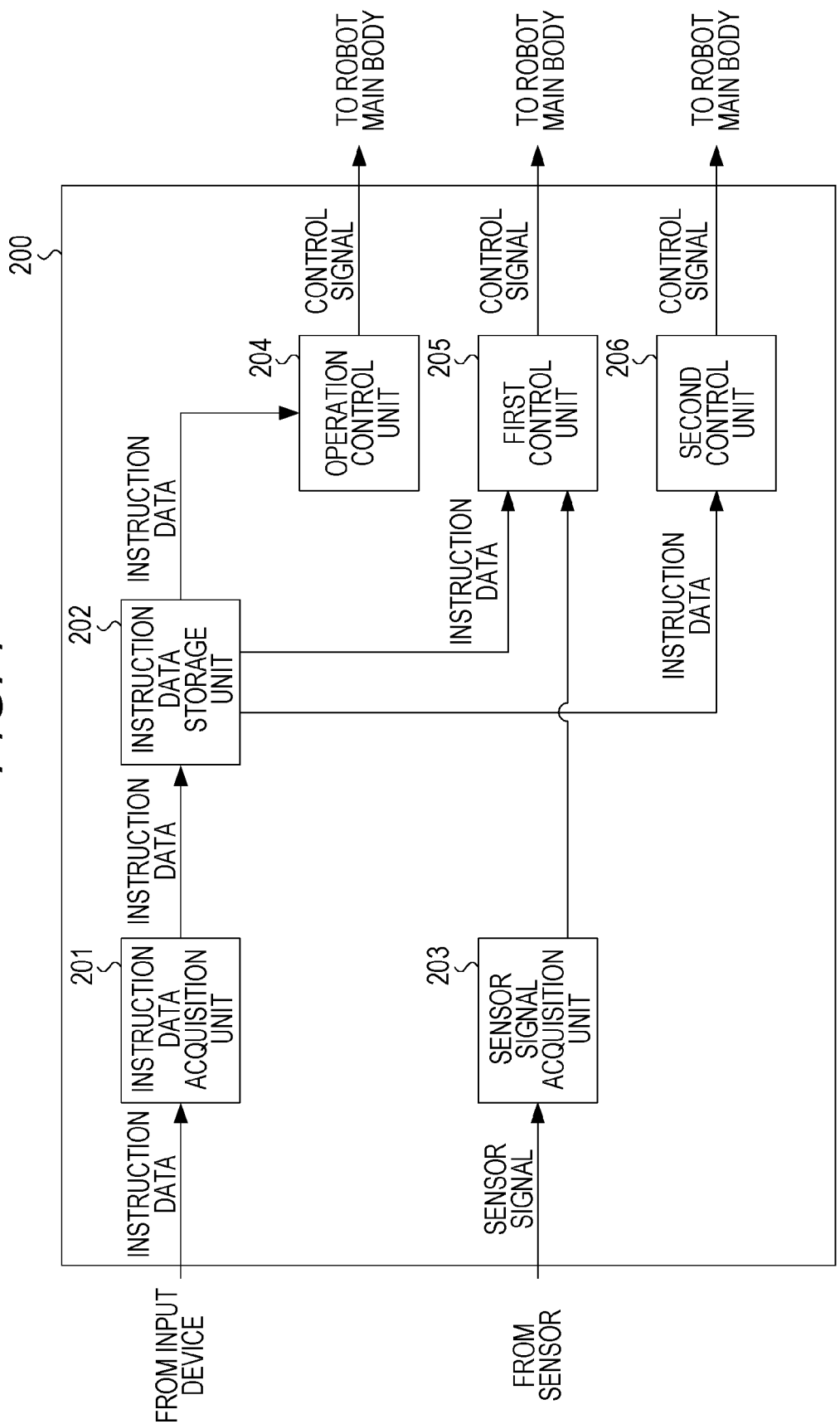
FIG. 7 is a function block diagram illustrating an example of a functional configuration of a robot controller.

Next, with reference to FIG. 7, an example of a mechanical configuration of the robot controller 200 is described.

As depicted in FIG. 7, the robot controller 200 includes an instruction data acquisition unit 201, an instruction data storage unit 202, a sensor signal acquisition unit 203, an operation control unit 204, a first control unit 205, and a second control unit 206.

In the robot system 1 of this embodiment, an instructor inputs instruction data related to the operation of the robot main body 100 using an appropriate input device. The instruction data acquisition unit 201 acquires the input instruction data and stores the data in the instruction data storage unit 202.

The sensor signal acquisition unit 203 acquires the above sensor signal output from the sensor 130 (result of detecting the tube 500 by the sensor 130).

The operation control unit 204 controls the operation of the entire robot main body 100 including the arms 103L and 103R and the hands 120L and 120R on the basis of the instruction data stored in the instruction data storage unit 202. For example, the operation controlled by the operation control unit 204 includes, for example, an operation of holding and releasing the tube 402 and the insertion tool 403 by the robot main body 100, an operation of opening and closing the lid 302 of the centrifugal separator 300, and an operation of the operation panel 310 of the centrifugal separator 300.

The first control unit 205 inputs the instruction data stored in the instruction data storage unit 202 and the sensor signal acquired by the sensor signal acquisition unit 203. The first control unit 205 controls the operation of the entire robot main body 100 including the arms 103L and 103R and the hands 120L and 120R on the basis of the instruction data and the sensor signal. For example, the first control unit 205 controls the robot main body 100 to insert the end part 403B of the insertion tool 403 into the insertion hole 306A provided on the rotor 305 of the centrifugal separator 300. After that, the first control unit 205 controls the robot main body 100 to move the inserted insertion tool 403 so that the rotation of the rotor 305 stops at a predetermined rotational position at which the position of the insertion hole 306B becomes a particular position.

The second control unit 206 controls the operation of the entire robot main body 100 including the arms 103L and 103R and the hands 120L and 120R on the basis of the instruction data stored in the instruction data storage unit 202. For example, it is assumed that the rotor 305 of the centrifugal separator 300 stops at the predetermined rotational position by the control of the first control unit 205. In this case, the second control unit 206 controls the robot main body 100 to insert the tube 402 into the insertion hole 306B of the rotor 305. Note that the insertion of the tube 402 into the insertion hole 306B corresponds to the installation of the tube 402 at the sample set part. In addition, it is assumed that the rotor 305 of the centrifugal separator 300 stops at the predetermined rotational position by the control of the first control unit 205 and that the rotor 305 has the tube 402 inserted into the insertion hole 306B of the rotor 305. In this case, the second control unit 206 can control the robot main body 100 to remove the tube 402 from the insertion hole 306B. Note that the removal of the tube 402 from the insertion hole 306B corresponds to the removal of the tube 402 from the sample set part.

Figure 8:
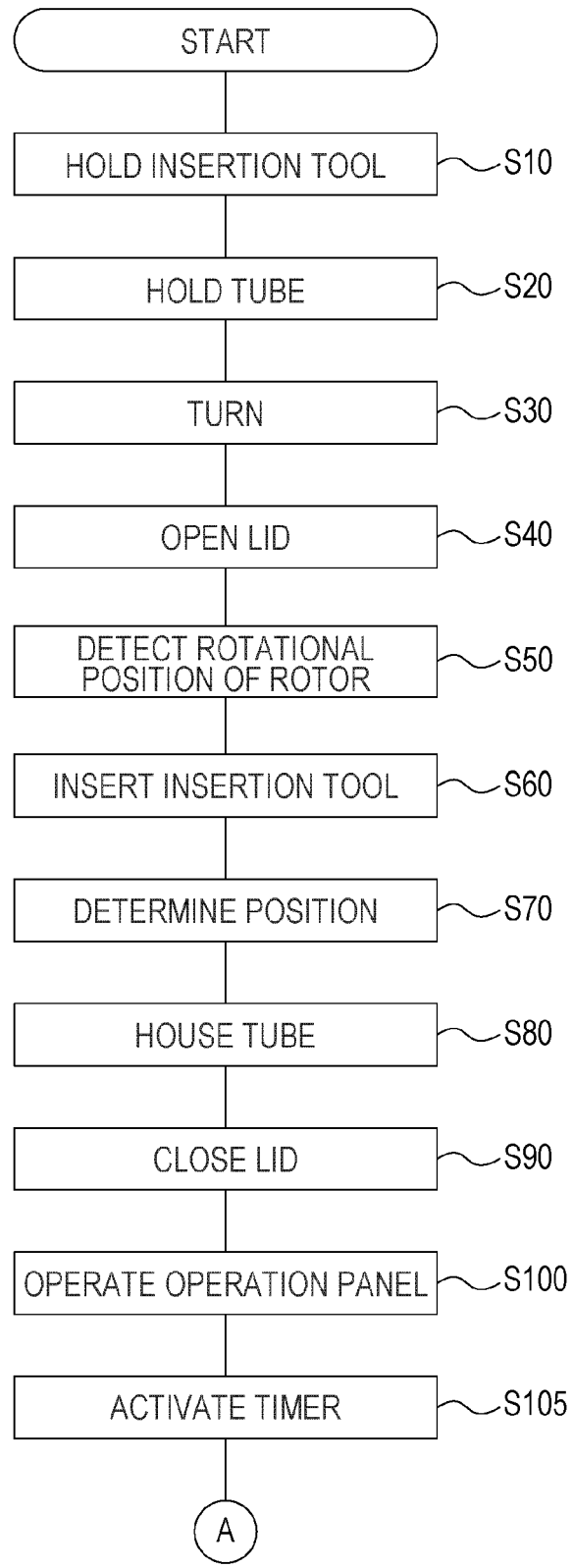
FIG. 8 is a flow chart of operation control over the robot main body by the robot controller.
Figure 9:
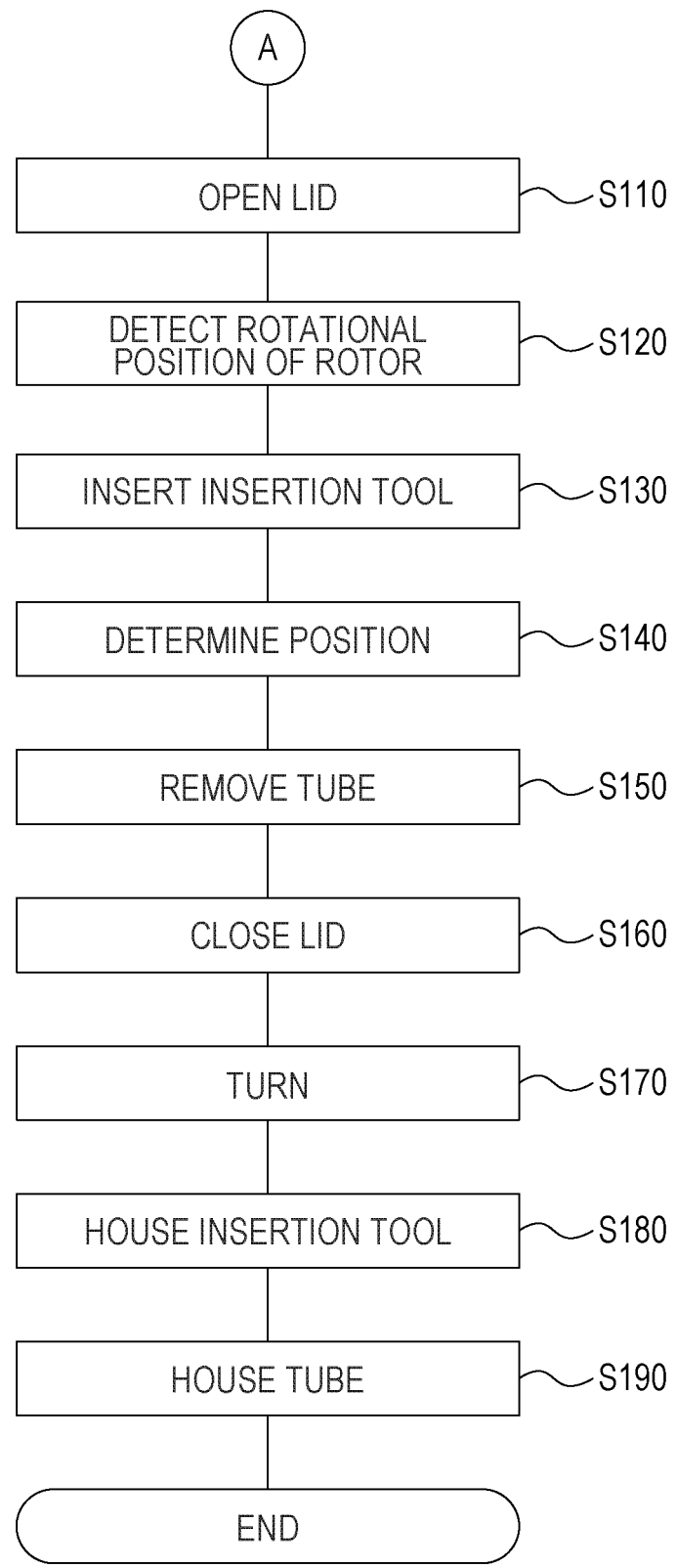
FIG. 9 is a flow chart of operation control over the robot main body by the robot controller.

Next, with reference to FIGS. 8 and 9, an example of the content of the operation control of the robot main body 100 by the robot controller 200 is described. Moreover, with reference to FIGS. 10 to 16, an example of the operation of the robot main body 100 by the control of the robot controller 200 is described. The tube 402 and the insertion tool 403 may be held by any of the two hands 120L and 120R of the robot main body 100. In the description below, the tube 402 is held by the left hand 120L while the insertion tool 403 is held by the right hand 120R.

The process in the flow chart of FIGS. 8 and 9 is started by the appropriate starting process. At the time of the start, the front of the robot main body 100 faces the table T. As depicted in FIG. 8, first, the operation control unit 204 operates the right arm 103R, the right hand 120R, and the like in Step S10 to allow the holding members 121 of the right hand 120R to hold the insertion tool 403 housed in the rack 401B on the table T.

After that, in Step S20, the operation control unit 204 operates the left arm 103L, the left hand 120L, and the like to allow the holding members 121 of the left hand 120L to hold the tube 402 housed in the rack 401A on the table T.

Then, in Step S30, the operation control unit 204 turns the trunk part 102 including the arms 103L and 103R so that the front of the robot main body 100 faces the centrifugal separator 300.

After that, in Step S40, the operation control unit 204 operates the right arm 103R, the right hand 120R, and the like to open the lid 302 of the centrifugal separator 300 with the right hand 120R. Note that the operation control unit 204 may open the lid 302 of the centrifugal separator 300 with the left hand 120L alternatively.

The rotor 305 of the centrifugal separator 300 stops at the appropriate rotational position. In Step S50, the operation control unit 204 operates the right arm 103R, the right hand 120R, and the like to allow the sensor 130 of the right hand 120R to detect the tube 500 in the insertion hole 306C of the rotor 305.

Figure 10:
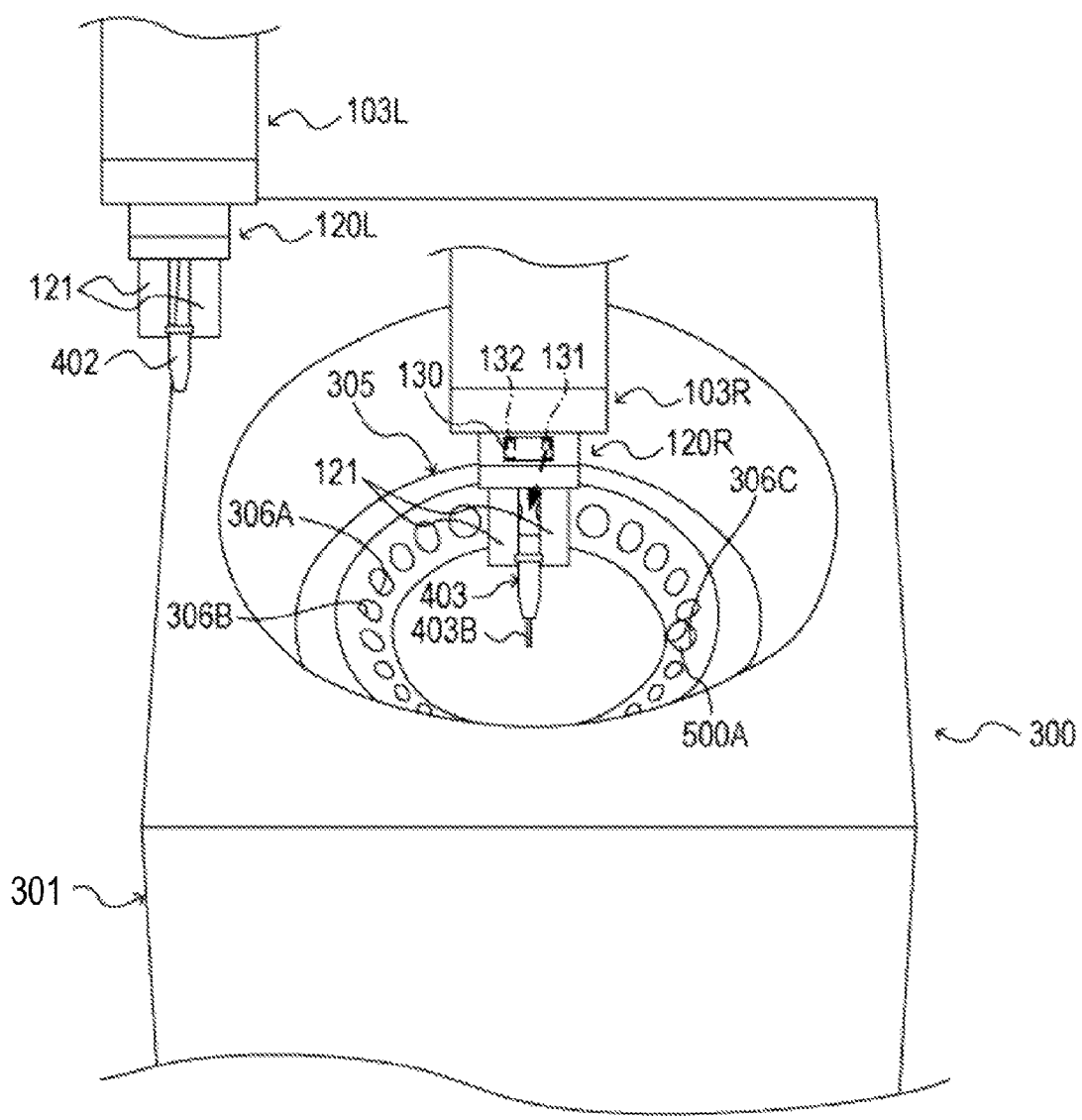
FIG. 10 is an explanatory diagram illustrating the operation of the robot main body.

For example, the operation control unit 204 moves the right hand 120R so that the sensor 130 is located above the rotor 305 as depicted in FIG. 10. The term "above" refers to the position where laser light from the light projection unit 131 of the sensor 130 (spot light in this example) is emitted to a region along the circumferential direction of a part of the rotor 305 which is provided with the 24 insertion holes 306. The operation control unit 204 rotates the moved right hand 120R along the circumferential direction of the rotor 305. Thus, the insertion holes 306 are sequentially irradiated with the laser light from the light projection unit 131 by the operation control unit 204.

Figure 11:
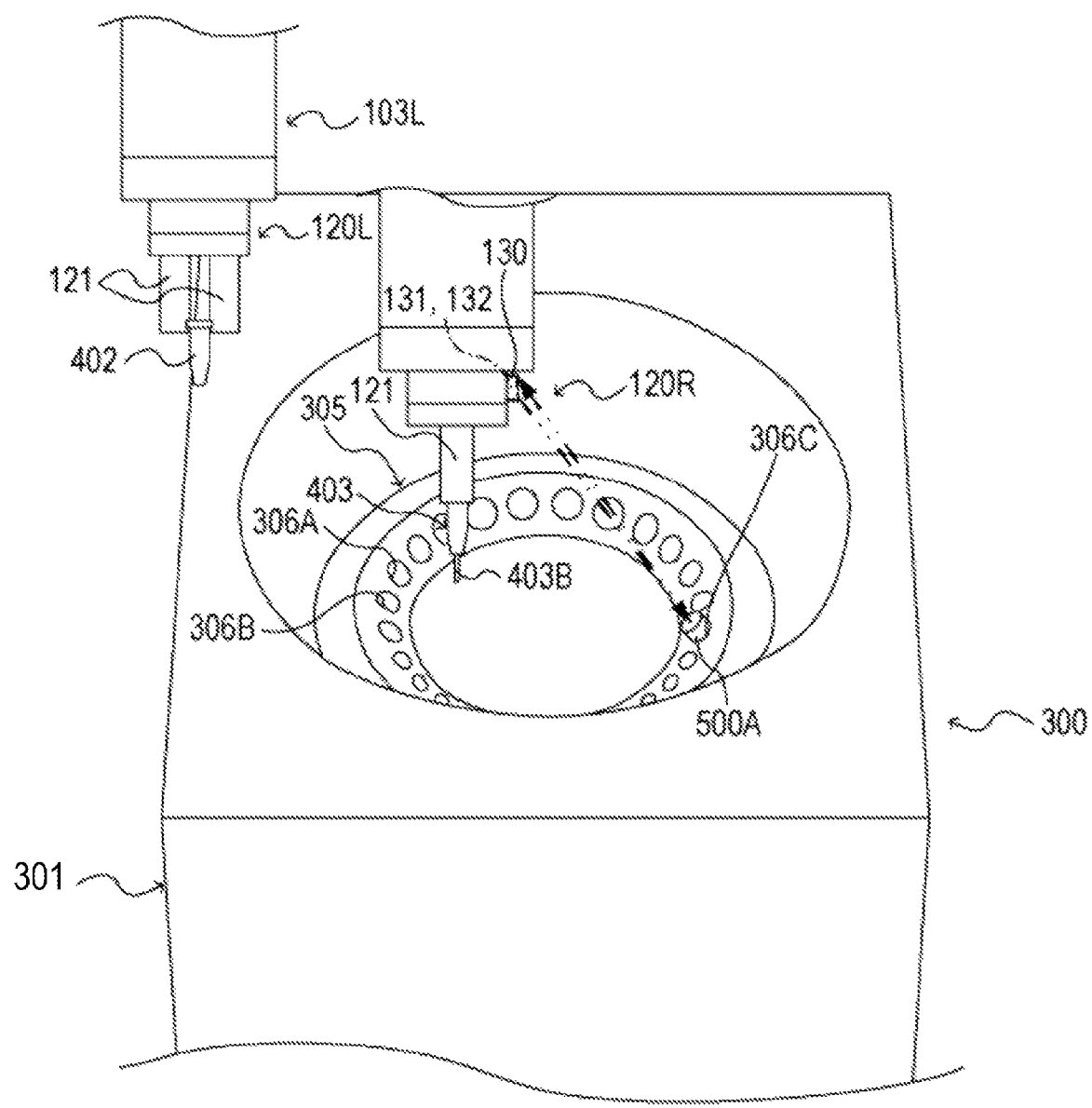
FIG. 11 is an explanatory diagram illustrating the operation of the robot main body.

At this time, as depicted in FIG. 11, the lid (lid part) 500A of the tube 500 in the insertion hole 306 is irradiated with the laser light from the light projection unit 131. The reflection light is received by the light reception unit 132. Thus, the tube 500 is detected. A sensor signal from the sensor 130 is acquired by the sensor signal acquisition unit 203. Therefore, the operation control unit 204 detects the position of the tube 500 on the basis of the sensor signal acquired by the sensor signal acquisition unit 203. As a result, the operation control unit 204 detects the rotational position of the rotor 305 stopping at the appropriate position (i.e., the position along the circumferential direction of each insertion hole 306 of the rotor 305). Based on the detection results, the insertion hole 306A is specified.

Figure 12:
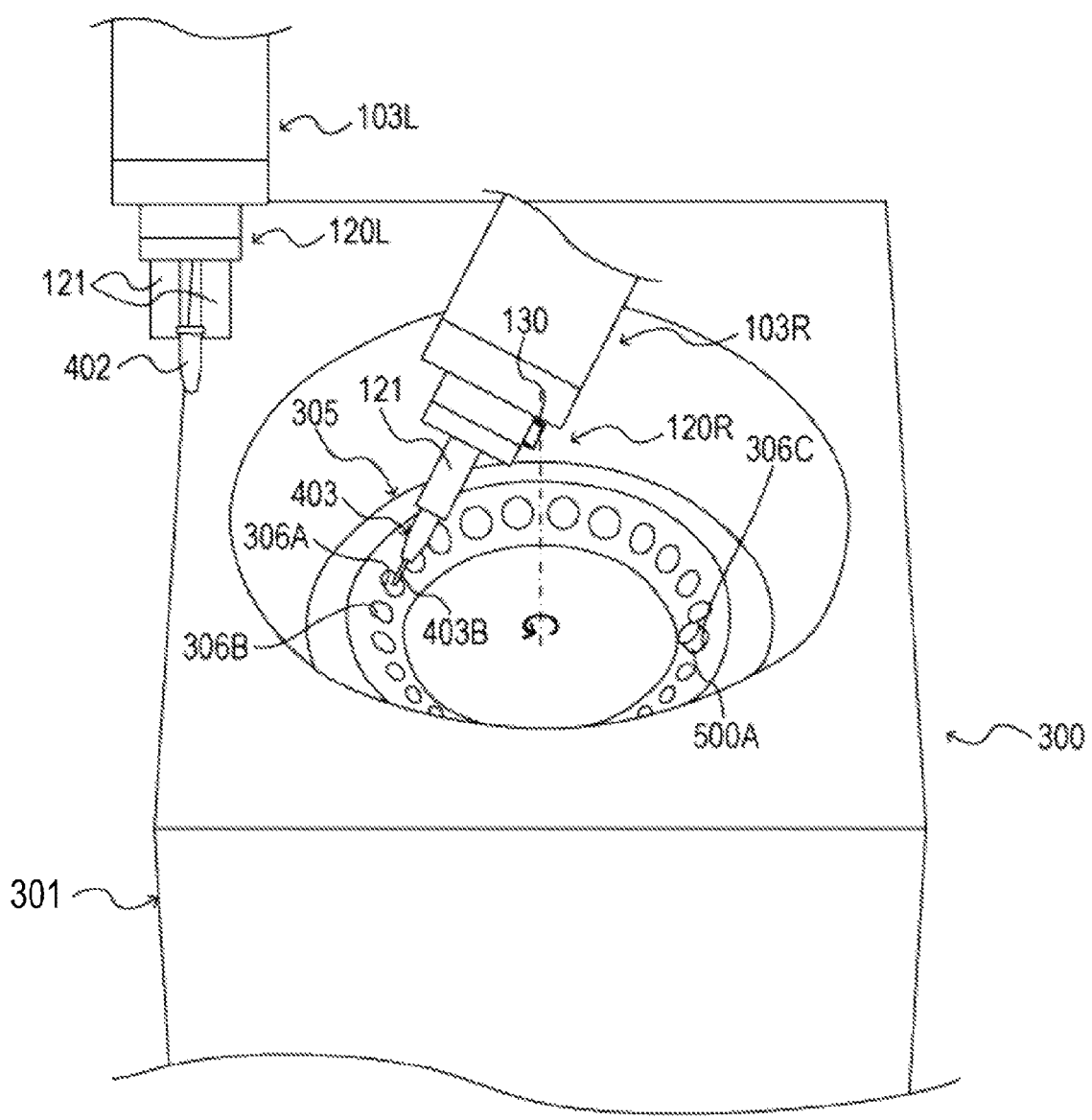
FIG. 12 is an explanatory diagram illustrating the operation of the robot main body.

After that, in Step S60, the first control unit 205 operates the right arm 103R, the right hand 120R, and the like to allow the end part 403B of the insertion tool 403 held by the holding members 121 of the right hand 120R to be inserted into the specified insertion hole 306A as depicted in FIG. 12.

Figure 13:
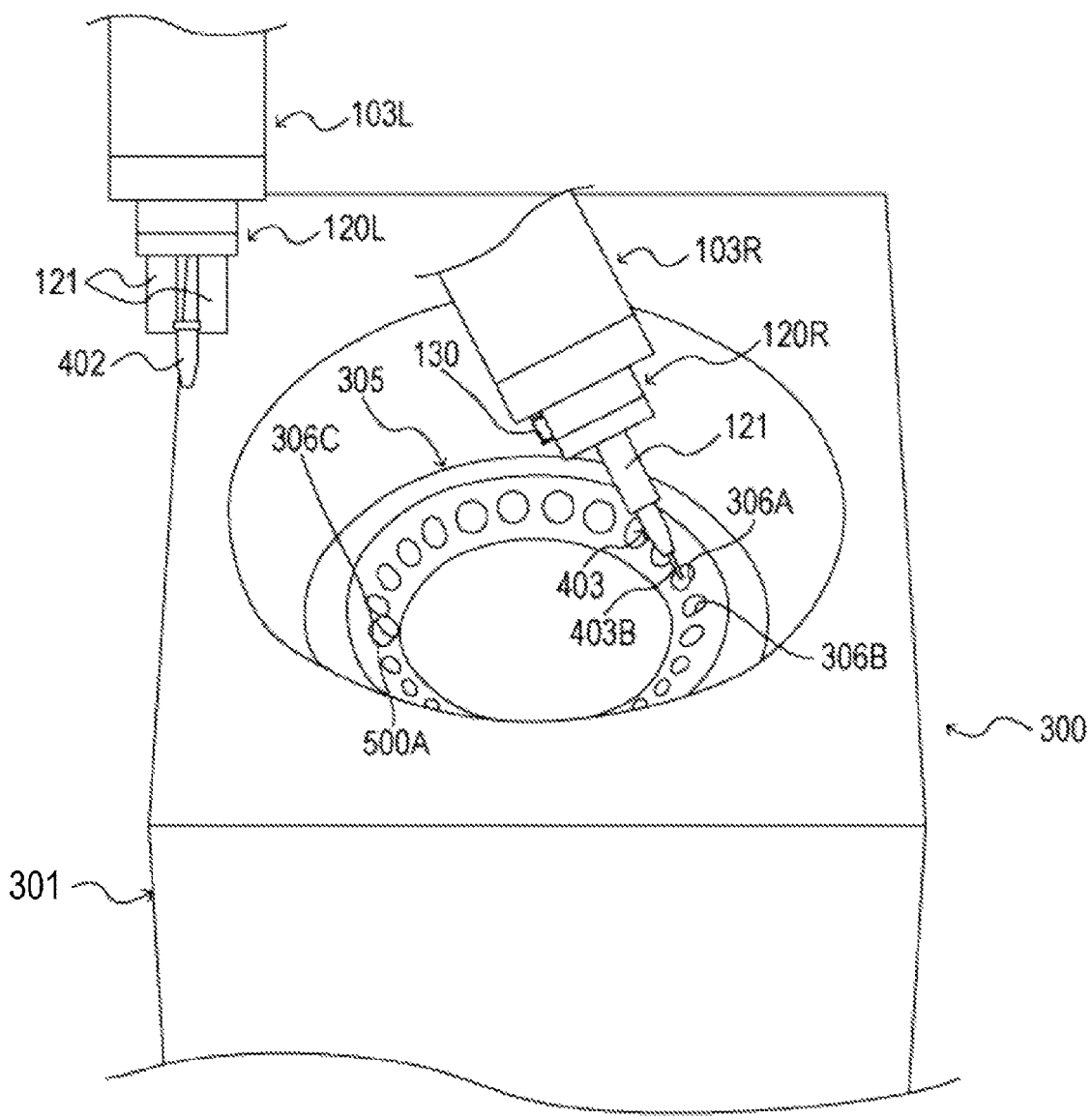
FIG. 13 is an explanatory diagram illustrating the operation of the robot main body.

Then, in Step S70, the first control unit 205 operates the right arm 103R, the right hand 120R, and the like to allow the insertion tool 403 inserted into the insertion hole 306A in Step S60 to move in one-side direction of the circumferential direction of the rotor 305 as depicted in FIG. 12 (counter-clockwise in the example depicted in FIG. 12). Thus, the first control unit 205 rotates the rotor 305, which has stopped at the appropriate position, up to a predetermined rotational position (position depicted in FIG. 13) and stops the rotor 305 at that position so that the position of the insertion hole 306B relative to the casing 301 becomes the predetermined specified position as depicted in FIG. 13. Thus, the rotational position of the rotor 305 and the position of the insertion hole 306B are determined.

Figure 14:
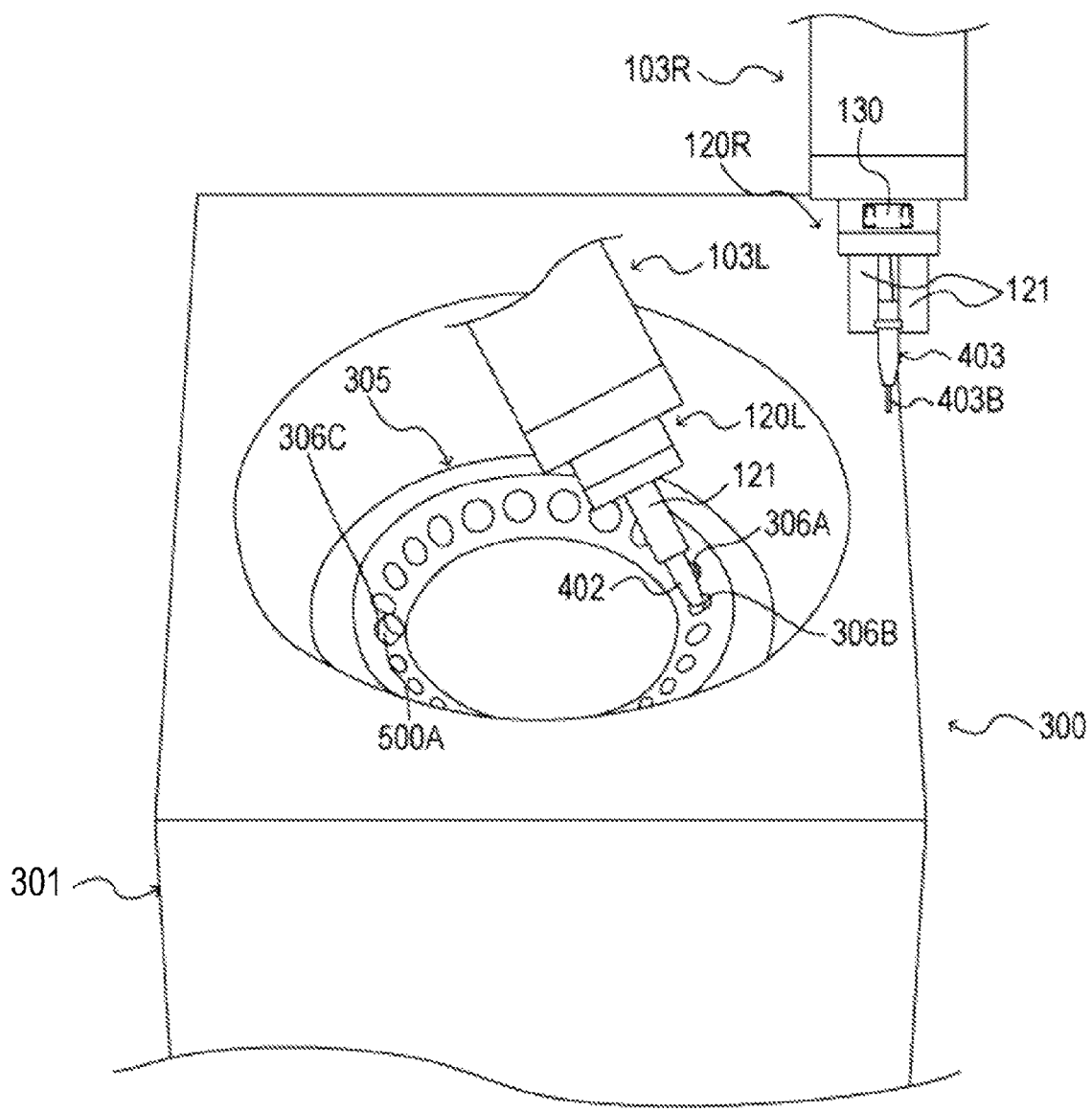
FIG. 14 is an explanatory diagram illustrating the operation of the robot main body.

After that, in Step S80, the second control unit 206 operates the left arm 103L, the left hand 120L, and the like to allow the tube 402, which is held by the holding members 121 of the left hand 120L, to be inserted into the insertion hole 306B of the rotor 305 stopping at the predetermined rotational position as depicted in FIG. 14. Then, the second control unit 206 causes the left hand 120L to release the tube 402. Thus, the tube 402 is housed in the insertion hole 306B.

Then, in Step S90, the operation control unit 204 operates the right arm 103R, the right hand 120R, and the like to close the lid 302 of the centrifugal separator 300 with the right hand 120R. Note that the operation control unit 204 may use the left hand 120L alternatively to close the lid 302 of the centrifugal separator 300.

After that, in Step S100, the operation control unit 204 operates the right arm 103R, the right hand 120R, and the like to operate the input unit of the operation panel 310 using the right hand 120R as appropriate. Thus, the operation control unit 204 starts the centrifugal separation process of the centrifugal separator 300. Note that the operation control unit 204 may start the centrifugal separation process of the centrifugal separator 300 by alternatively operating the input unit of the operation panel 310 using the left hand 120L as appropriate.

The robot main body 100 is provided with a timer (not shown). The set time of the timer is approximately equal to the time from the start to the end of the centrifugal separation process of the centrifugal separator 300. In Step S105, the operation control unit 204 activates the timer. Thus, the operation control unit 204 makes the robot main body 100 standby during the set time of the timer.

Note that the centrifugal separator 300 and the robot controller 200 may be connected to each other. In this case, the centrifugal separator 300 may be set so that the signal is output to the robot controller 200 at the time of the end of the centrifugal separation process. The robot controller 200 may have the robot main body 100 standby until the signal is input.

After the centrifugal separation process of the centrifugal separator 300 ends, that is, after the set time of the timer activated in Step S105 has passed, the operation control unit 204 operates the right arm 103R, the right hand 120R, and the like in Step S110 to open the lid 302 of the centrifugal separator 300 with the right hand 120R like in Step S40 as depicted in FIG. 9.

The rotor 305 of the centrifugal separator 300 stops at the appropriate rotational position. In Step S120, the operation control unit 204 operates the right arm 103R, the right hand 120R, and the like to allow the sensor 130 of the right hand 120R to detect the tube 500 in the insertion hole 306C of the rotor 305 like in Step S50. On this occasion, the rotor 305 has the tube 402 and the tube 500 housed therein. For example, the longitudinal size of the tube 500 may be larger than that of the tube 402. In other words, the amount of the tube 500 protruding out of the insertion hole 306C may be larger than the amount of the tube 402 protruding out of the insertion hole 306B. Moreover, the reflectivity of the laser light at the lid 500A of the tube 500 may be higher than that of the laser light at the lid 402A of the tube 402. This facilitates the detection of the tube 500. Thus, the operation control unit 204 detects the position of the tube 500 on the basis of the sensor signal acquired by the sensor signal acquisition unit 203. Thus, the operation control unit 204 detects the rotational position of the rotor 305 stopping at the appropriate position (i.e., the position along the circumferential direction of each insertion hole 306 of the rotor 305). Based on this detection results, the insertion hole 306A is specified.

Figure 15:
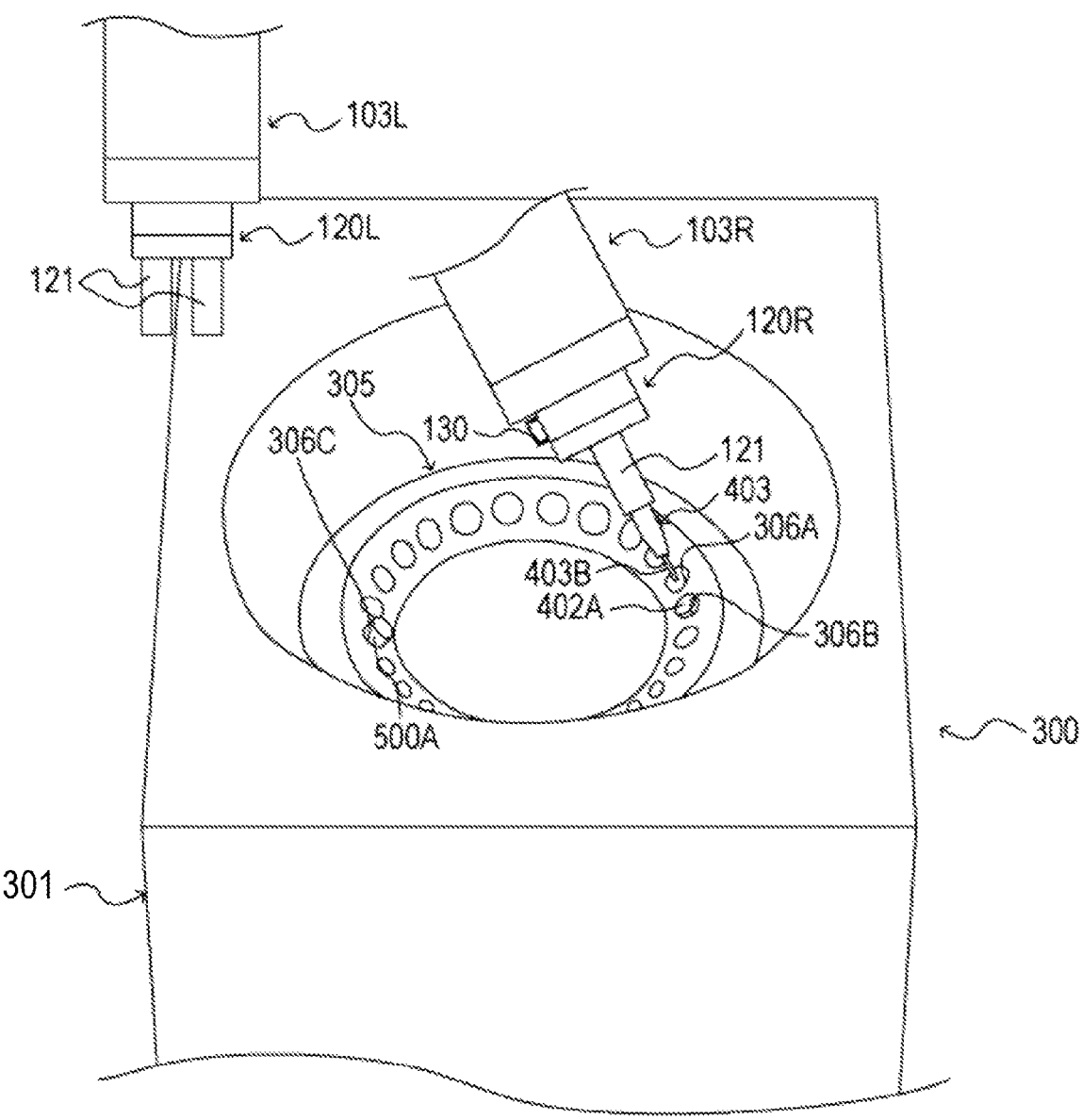
FIG. 15 is an explanatory diagram illustrating the operation of the robot main body.

Then, in Step S130, the first control unit 205 operates the right arm 103R, the right hand 120R, and the like to allow the end part 403B of the insertion tool 403 held by the right hand 120R to be inserted into the specified insertion hole 306A as depicted in FIG. 15 like in Step S60.

After that, in Step S140, the first control unit 205 operates the right arm 103R, the right hand 120R, and the like to allow the insertion tool 403 inserted into the insertion hole 306A in Step S130 to move in one-side direction of the circumferential direction of the rotor 305 like in Step S70. Thus, the first control unit 205 rotates the rotor 305 stopping at the appropriate position up to the predetermined rotational position. This determines the rotational position of the rotor 305.

Figure 16:
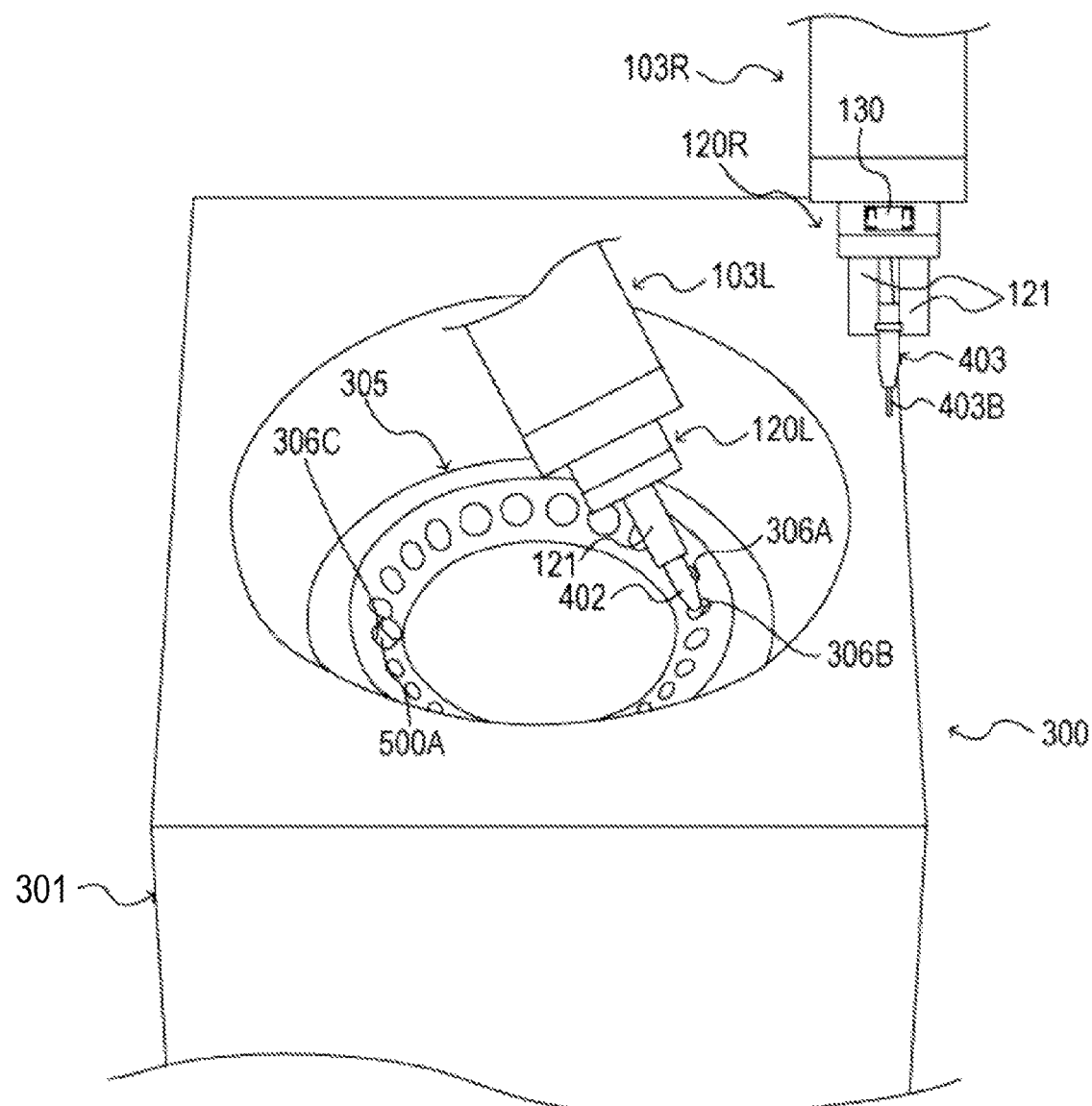
FIG. 16 is an explanatory diagram illustrating the operation of the robot main body.

Then, in Step S150, the second control unit 206 operates the left arm 103L, the left hand 120L, and the like to allow the holding members 121 of the left hand 120L to hold the tube 402 in the insertion hole 306B of the rotor 305 stopping at the predetermined rotational position and to remove tube 402 from the insertion hole 306B as depicted in FIG. 16.

After that, in Step S160, the operation control unit 204 operates the right arm 103R, the right hand 120R, and the like to close the lid 302 of the centrifugal separator 300 with the right hand 120R like in Step S90.

Then, in Step S170, the operation control unit 204 turns the trunk part 102 and the like so that the front of the robot main body 100 faces the table T.

After that, in Step S180, the operation control unit 204 operates the right arm 103R, the right hand 120R, and the like to insert the insertion tool 403 held by the holding members 121 of the right hand 120R into the rack 401B on the table T. After that, the operation control unit 204 causes the holding members 121 to release the insertion tool 403. Thus, the insertion tool 403 is housed in the rack 401B.

Then, in Step S190, the operation control unit 204 operates the left arm 103L, the left hand 120L, and the like to insert the tube 402 held by the holding members 121 of the left hand 120L into the rack 401A on the table T. After that, the operation control unit 204 causes the holding members 121 to release the tube 402. Thus, the tube 402 is housed in the rack 401A. Then, the process in the flow chart ends.

As thus described, the robot system 1 according to this embodiment performs installation and removal of the tube 402 at and from the rotor 305 in the centrifugal separation process of the centrifugal separator 300 with respect to the sample Sa in the tube 402. In the centrifugal separator 300, the rotor 305 is rotatably supported by the casing 301. A part of the rotor 305 where the tube 402 is installed and removed (sample set part) is fixedly determined in advance. The rotational position of the rotor 305 might vary (might not be constant) every time the centrifugal separation process ends. Therefore, the position of the sample set part of the rotor 305 is not constant either every time the centrifugal separation process ends.

In the robot system 1 of this embodiment, the first control unit 205 controls the operation of the arms 103L and 103R and the hands 120L and 120R. Thus, the first control unit 205 sets the rotational position of the rotor 305, which is not constant, at the particular position. That is, the tube 500 in the insertion hole 306C of the rotor 305 is detected by the sensor 130. The insertion tool 403 held by the hands 120L and 120R is inserted into the insertion hole 306B of the rotor 305. The first control unit 205 rotates the rotor 305 in accordance with the detection results of the sensor 130. Thus, the rotational position of the rotor 305 is set at the predetermined rotational position. Then, the second control unit 206 controls the arms 103L and 103R and the hands 120L and 120R. Thus, the second control unit 206 performs the installation and removal of the tube 402 at and from the sample set part of the rotor 305 stopping at the particular position (the above predetermined rotational position).

As aforementioned, in this embodiment, wherever the rotor 305 stops, the control by the first control unit 205 can set the rotational position of the rotor 305 at the particular position. Thus, with the robot main body 100, the installation and removal of the tube 402 at and from the sample set part can be performed with respect to the sample set part at approximately the same position on the basis of the subsequent control by the second control unit 206. As a result, it is no longer necessary to specify the rotational position of the rotor and the sample set part through photographing and/or image analysis or the like every time for the installation and the removal of the tube 402. Thus, the operation control of the robot main body 100 can be simplified. Moreover, the reliability of the operation of the robot main body 100 can be increased.

In this embodiment, after the insertion tool 403 is inserted into the insertion hole 306A, the first control unit 205 operates the inserted insertion tool 403. Thus, the first control unit 205 sets the rotational position of the rotor 305 at the predetermined rotational position so that the sample set part of the rotor 305 is at the particular position. To achieve this, the first control unit 205 controls the operation of the arms 103L and 103R and the hands 120L and 120R. In this manner, in this embodiment, the first control unit 205 moves the insertion tool 403 inserted into the insertion hole 306A in the circumferential direction of the rotor 305 without any change. As a result, the rotational position of the rotor 305 can be set at the predetermined rotational position easily and smoothly.

Moreover, in this embodiment, the first control unit 205 controls the operation of the arms 103L and 103R and the hands 120L and 120R to rotate the rotor 305 up to the predetermined rotational position so that the insertion hole 306B of the rotor 305 as the sample set part comes to the particular position. Thus, wherever the rotational position (stop position) of the rotor 305 is, the position of the insertion hole 306B can be set at the particular position. As a result, the robot main body 100 can perform the insertion and removal of the tube 402 into and from the insertion hole 306B at approximately the same position in the centrifugal separation process. That is, the relative positional relationship between the robot main body 100 and the insertion hole 306B can be approximately the same easily.

In this embodiment, the rotor 305 stops at the predetermined rotational position by the control of the first control unit 205. The second control unit 206 controls the operation of the arms 103L and 103R and the hands 120L and 120R so that the tube 402 is inserted into the insertion hole 306B of the rotor 305 or the inserted tube 402 is removed from the insertion hole 306B. Thus, wherever the rotor 305 stops, the robot main body 100 can insert or remove the tube 402 into or from the insertion hole 306B at approximately the same position with high accuracy.

In this embodiment, the insertion hole 306B of the rotor 305 is a hole used for inserting and removing the tube 402. Meanwhile, the insertion hole 306C is provided on the rotor 305 like the insertion hole 306B. This insertion hole 306C is a hole used for inserting and removing the tube 500 serving as the positioning member. The sensor 130 detects the tube 500 inserted into this insertion hole 306C. Thus, the rotational position can be detected using the insertion hole 306C in this embodiment. The insertion hole 306B and the insertion hole 306C may be shared. In this case, the appropriate ones of the insertion holes 306 of the rotor 305 may be used as the insertion hole 306B and the insertion hole 306C. The positional relationship between the insertion hole 306B and the insertion hole 306C may be set as appropriate. In this case, the weight balance of the rotor 305 can be set as desired considering the weight of the tube 402 inserted into the insertion hole 306B and the weight of the tube 500 inserted into the insertion hole 306C.

In this embodiment, the centrifugal separator 300 centrifugally separates the sample Sa inside the tube 402. On this occasion, wherever the rotor 305 stops, the installation and removal of the tube 402 at and from the rotor 305 can always be performed at the same position. As a result, the reliability of the operation of the centrifugal separator 300 can be increased.

The embodiment of the present disclosure is not limited to the above description. The present disclosure can be modified within the range not departing from the content and technical thought thereof. In the above embodiment, the insertion tool 403 held by the hands 120L and 120R is inserted into the insertion hole 306A. After that, by moving the inserted insertion tool 403, the rotor 305 is rotated. However, the present disclosure is not limited thereto; for example, the hand may have a finger member, a projection, or the like. By inserting any of these into the insertion port and moving it, the rotor may be rotated. Alternatively, the rotor may be rotated by holding and moving the projection or the like of the rotor with the finger member or the like. Further alternatively, the rotor may be rotated by pushing and moving the rotor with the finger member or the like.

In this embodiment, the sensor 130 detects the tube 500 inserted into the insertion hole 306C of the rotor 305. Thus, the rotational position of the rotor 305 is detected. However, for example, the rotational position of the rotor may be detected by detecting an appropriate mark on the rotor (for example, an optical mark or a magnetic mark) with an appropriate detection unit (for example, an optical sensor or a magnetic sensor).

In the above embodiment, the robot main body 100 serves as a double-arm robot having the two arms 103L and 103R and the two hands 120L and 120R. However, the embodiment of the present disclosure is not limited to this example. For example, the robot main body may be a single-arm robot having one arm and one hand or a robot having three or more arms and three or more hands.

In the above embodiment, the rotor 305 is provided with one tube 402. The centrifugal separator 300 processes one sample Sa in one operation. However, the embodiment of the present disclosure is not limited to this example. For example, the robot system may have the rotor 305 with the two or more tubes 402 so that the centrifugal separator 300 can process two or more samples Sa in one operation.

In the above embodiment, the robot system 10 performs a series of jobs including a job of inserting the tube 402 into the insertion hole 306 provided on the rotor 305 of the centrifugal separator 300 and a job of removing the tube 402 from the insertion hole 306. However, the embodiment of the present disclosure is not limited to this example. The robot system according to the present disclosure may be a device performing a predetermined process (for example, exhibition using a Ferris wheel) on a work using a rotation device (for example, a demonstrator like a Ferris wheel) other than the centrifugal separator.

The arrow in FIG. 7 indicates one example of the flow of the signal. This arrow does not limit the direction where the signal flows.

The flow charts of FIGS. 8 and 9 do not limit the embodiment to the procedure shown in these charts. The procedure in the charts may be added, deleted, or modified within the range not departing from the content and technical thought of the present disclosure.

The methods in the embodiment and each modified example may be combined with each other as appropriate.

Although not exemplified, various modifications may be made in the embodiment and each modified example within the range not departing from the content.

In Step S105, the operation control unit 204 activates the timer (not shown) of the robot main body 100 which is set to approximately the same time as the end timing of the centrifugal separation process of the centrifugal separator 300 started in Step S100, and the robot main body 100 is made standby until the end of the set time of the timer. Note that the centrifugal separator 300 and the robot controller 200 may be connected to each other and the centrifugal separator 300 may be set so that the signal is output to the robot controller 200 upon the end of the centrifugal separation process, and the robot main body 100 may be kept standby until the signal is input. In this embodiment, wherever the rotor 305 stops, the control by the first control unit 205 can make the rotational position of the rotor 305 uniform at the particular position. Thus, the installation and removal of the tube 402 at and from the sample set part on the basis of the subsequent control by the second control unit 206 can always be performed at the same position from the view of the robot main body 100. As a result, as compared with the case where the tube 402 is installed and removed through the photographing, image analysis, and the like every time with respect to the unstable rotational position and sample set part, the operation control of the robot main body 100 can be simplified and the operation reliability can be increased. Moreover, the robot system according to the present disclosure may be any of the following first to sixth robot systems.

A first robot system includes: at least one robot arm; at least one robot hand provided on the at least one robot arm; a contact unit provided on the at least one robot hand to be in contact with a rotator body, which is capable of housing a work, of a rotator device which includes the rotator body and a fixed part for rotatably supporting the rotator body and which performs a predetermined process on the work; a detection unit configured to detect a detection target part provided on the rotation body; a first control unit for controlling operation of the robot arm and the robot hand so that the contact unit is brought into contact with the rotation body and rotates the rotation body up to a predetermined rotational position according to a result of detecting the detection target part by the detection unit; and a second control unit configured to control operation of the robot arm and the robot hand so that the work is installed at a predetermined work set part of the rotation body stopping at the predetermined rotational position by the control of the first control unit or the work is removed from the work set part.

A second robot system is the first robot system in which: the contact unit is the robot hand or an insertion tool held by the robot hand, which can be inserted into a first insertion port provided on the rotation body of the rotation device; and the first control unit controls the operation of the robot arm and the robot hand so that, after the insertion of the robot hand or the insertion tool into the first insertion port, the rotation body is rotated up to the predetermined rotational position at which the work set part of the rotation body becomes a predetermined particular position relative to the fixed unit by moving the inserted robot hand or insertion tool.

A third robot system is the second robot system in which: the first control unit controls the operation of the robot arm and the robot hand so that the rotation body is rotated up to the predetermined rotational position at which a second insertion port provided on the rotation body as the work set part comes to the particular position.

A fourth robot system is the third robot system in which: the second control unit controls the operation of the robot arm and the robot hand so that work is inserted into the second insertion port of the rotation body stopping at the predetermined rotational position by the control of the first control unit or the work is removed from the second insertion port.

A fifth robot system is any of the second to fourth robot systems in which: the detection unit is a sensor for detecting a positioning member serving as the detection target part inserted into a third insertion port among plural insertion ports provided on the rotation body.

A sixth robot system is any of the first to fifth robot systems in which: the rotation device is a centrifugal separator for performing centrifugal separation as the predetermined process; and the work is a vessel to be processed in which a body to be separated as the target of the centrifugal separation is housed.

According to the first to sixth robot systems, the operation control of the robot arm and the robot hand can be simplified and the operation reliability thereof can be increased.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A method of controlling a robot comprising a robot arm and a robot hand provided on the robot arm, the method comprising:

performing a first operation of the robot arm and the robot hand to detect a detection target part provided on a rotation body of a rotation device using a sensor, the rotation device includes the rotation body capable of housing a vessel and a fixed part rotatably supporting the rotation body, the rotation body includes a first insertion port and a second insertion port which are to house the vessel;

performing a second operation of the robot arm and the robot hand so that an insertion tool is inserted into the first insertion port, the insertion tool is provided on the robot hand, the first insertion port is specified based on a result of the first operation;

performing a third operation of the robot arm and the robot hand to move the insertion tool inserted into the first insertion port so that a rotational position of the rotation body is set at a predetermined rotational position at which a position of the second insertion port relative to the fixed part becomes a predetermined particular position; and performing a fourth operation of the robot arm and the robot hand so that the vessel is inserted into or removed from the second insertion port of the rotation body when the rotation body is stopped at the predetermined rotational position.

2. A robot system comprising:

a robot arm;

a robot hand provided on the robot arm;

a rotation device configured to perform a predetermined process on a work, the rotation device having a rotation body capable of housing a vessel and a fixed part rotatably supporting the rotation body, the rotation body having a plurality of insertion holes;

a means for rotating the rotation body provided on the robot hand;

a means for detecting a detection target part provided on the rotation body, the means for detecting a detection target part being provided on the robot hand;

a means for controlling a first operation of the robot arm and the robot hand to detect the detection target part by the means for detecting the detection target part; and a means for controlling a second operation of the robot arm and the robot hand so that the vessel is inserted into or removed from a predetermined insertion hole of the plurality of insertion holes when the rotation body is stopped at a predetermined rotational position.

3. A robot system comprising:

a robot arm;

a robot hand provided on the robot arm;

a rotation device configured to perform a predetermined process on a work, the rotation device having a rotation body capable of housing a vessel and a fixed part rotatably supporting the rotation body, the rotation body having a plurality of insertion holes;

an insertion tool provided on the robot hand for rotating the rotation body;

a sensor provided on the robot hand, the sensor being configured to detect a detection target part provided on the rotation body; and a controller configured to control a first operation of the robot arm and the robot hand to detect the detection target part by the sensor, wherein the controller is configured to control a second operation of the robot arm and the robot hand so that the vessel is inserted into or removed from a predetermined insertion hole of the plurality of insertion holes when the rotation body is stopped at a predetermined rotational position.

4. The robot system according to claim 3,
wherein the plurality of insertion holes includes a first insertion port and a second insertion port different from the first insertion port,
wherein the insertion tool is insertable into the first insertion port specified based on the result of the detection target part by the sensor,
wherein the controller is configured to control a third operation of the robot arm and the robot hand so that the insertion tool is inserted into the first insertion port, and
wherein the controller is configured to set a rotation position of the rotation body at the predetermined rotational position at which a position of the second insertion port relative to the fixed part becomes a predetermined particular position by controlling a fourth operation of the robot arm and the robot hand to move the insertion tool inserted into the first insertion port.

5. The robot system according to claim 4, wherein the insertion tool is held by the robot hand.

6. The robot system according to claim 4 wherein the second insertion port is the predetermined insertion hole.

7. The robot system according to claim 3, wherein the plurality of insertion holes includes a third insertion port, and
the sensor detects a positioning member serving as the detection target part, which is inserted into the third insertion port.

8. The robot system according to claim 7, wherein the second insertion port is provided at a position facing the third insertion port.

9. The robot system according to claim 3, wherein the rotation device is a centrifugal separator for performing centrifugal separation as the predetermined process, and
the work is the vessel which houses a body to be separated as a target of centrifugal separation.

10. The robot system according to claim 3, wherein the robot hand includes a first hand and a second hand,
the insertion tool is provided on the first hand, and
the second hand is configured to install the vessel or remove the vessel.

\* \* \* \* \*